United States Patent
Xu et al.

(10) Patent No.: US 12,412,367 B2
(45) Date of Patent: Sep. 9, 2025

(54) OPERATING ROOM OBJECTS AND WORKFLOW TRACKING USING DEPTH CAMERAS

(71) Applicant: Verb Surgical Inc., Santa Clara, CA (US)

(72) Inventors: Yiming Xu, Sunnyvale, CA (US); Bernhard Fuerst, Sunnyvale, CA (US); Genevieve Foley, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 620 days.

(21) Appl. No.: 17/741,812

(22) Filed: May 11, 2022

(65) Prior Publication Data
US 2023/0368492 A1    Nov. 16, 2023

(51) Int. Cl.
*G06V 10/762* (2022.01)
*G06T 7/20* (2017.01)
(Continued)

(52) U.S. Cl.
CPC .............. *G06V 10/762* (2022.01); *G06T 7/20* (2013.01); *G06T 7/50* (2017.01); *G06T 7/60* (2013.01);
(Continued)

(58) Field of Classification Search
CPC ...... G06V 10/762; G06V 20/52; G06V 10/62; G06V 10/763; G06V 20/64; G06V 40/103; G06T 7/20; G06T 7/50; G06T 7/60; G06T 7/70; G06T 7/80; G06T 2207/10028; G06T 2207/30232; G06T 7/292; G06T 2207/10024; G06T 2207/20084;
(Continued)

(56) References Cited

U.S. PATENT DOCUMENTS 10,395,123 B2   8/2019   Franz et al.
10,535,146 B1   1/2020   Buibas et al.
(Continued)

OTHER PUBLICATIONS

"Camera Calibration with OpenCV," OpenCV, retrieved from the Internet on May 11, 2022, <https://docs.opencv.org/2.4/doc/tutorials/calib3d/camera_calibration/camera_calibration.html>, 11 pages.

*Primary Examiner* — John Villecco
*Assistant Examiner* — Han Hoang
(74) *Attorney, Agent, or Firm* — Aikin & Gallant, LLP

(57) ABSTRACT

Embodiments described herein provide systems and techniques for tracking workflow inside an operating room (OR) by identifying and tracking target objects, such as a patient bed or a surgical table in the OR. In one aspect, a process for identifying and tracking a target object in an OR begins by receiving a depth image among a sequence of depth images captured by a depth camera installed in the OR. The process then generates a three-dimensional (3D) point cloud based on the depth image. Next, the process identifies a set of potential target points in the 3D point cloud that potentially belongs to the target object based on one or more target object criteria. The process next extracts one or more object clusters of from the set of potential target points using a data-point clustering technique. The process subsequently identifies the target object from the extracted one or more object clusters.

18 Claims, 9 Drawing Sheets
(2 of 9 Drawing Sheet(s) Filed in Color)

(51) Int. Cl.
  *G06T 7/50* (2017.01)
  *G06T 7/60* (2017.01)
  *G06T 7/70* (2017.01)
  *G06T 7/80* (2017.01)
  *G06V 20/52* (2022.01)
  *G16H 40/20* (2018.01)

(52) U.S. Cl.
  CPC .............. *G06T 7/70* (2017.01); *G06T 7/80* (2017.01); *G06V 20/52* (2022.01); *G16H 40/20* (2018.01); *G06T 2207/10028* (2013.01); *G06T 2207/30232* (2013.01)

(58) Field of Classification Search
  CPC . G06T 2207/30004; G06T 2207/30196; G06T 7/246; G16H 40/20; G16H 30/40
  See application file for complete search history.

(56) References Cited

U.S. PATENT DOCUMENTS

| | | | |
|---|---|---|---|
| 2016/0267327 A1* | 9/2016 | Franz | A61B 5/0077 |
| 2021/0195120 A1* | 6/2021 | King | H04N 5/272 |
| 2021/0256705 A1* | 8/2021 | Yu | G06V 10/44 |
| 2022/0080060 A1* | 3/2022 | Jarvis | G16H 40/67 |
| 2022/0189119 A1* | 6/2022 | Seo | G06T 7/00 |
| 2023/0306629 A1* | 9/2023 | Cho | G06T 7/33 |
| 2023/0360322 A1* | 11/2023 | Majewski | G06T 5/70 |

* cited by examiner

OPERATING ROOM OBJECTS AND WORKFLOW TRACKING USING DEPTH CAMERAS

TECHNICAL FIELD

The disclosed embodiments generally relate to computer-vision and machine-learning (ML) techniques for improving operating room (OR) workflow efficiencies. More specifically, the disclosed embodiments relate to identifying and tracking target objects during surgeries using a depth camera for OR workflow management.

BACKGROUND

Operating room (OR) costs are among one of the highest medical and healthcare-related costs in the US. With skyrocketing healthcare expenditures, OR-costs management aimed at reducing OR costs and increasing OR efficiency has become an increasingly important research subject. One sure way to improve OR efficiency is to optimize the utilization of OR resources. Many hospitals manage multiple operating rooms at the same time and have hospital staff fill various roles on an ever-changing schedule due to various factors. To achieve efficient resource allocation and staff assignment, it is important to maintain a robust system for communication and coordination. Majority of the OR responsibilities are taken by circulator nurses, who not only need to prepare for surgical tools and materials and to monitor and escort the patients, but also keep track of the OR schedules and workflows. However, hospitals are also increasingly exploring digital solutions that use sensor/camera systems to facilitate and automate tracking and scheduling OR workflows.

For example, there are a number of existing sensor-based techniques for identifying and tracking patients entering and exiting OR. One such solution is to attach wireless electronic tags or trackers (e.g., in the form of wrist bands) to track patients wirelessly. These wireless options, from lower-cost Bluetooth devices or radio-frequency identification (RFID) tags to higher-cost transponders provide positional information with varying accuracy and robustness. However, wireless-sensor options having desirable performances are often on the expensive side. Moreover, having an attachment to the patient can interfere with the OR workflow and add complexity to the procedure protocols, because such attachments usually need be removed during surgery preparation.

Another digital solution is to use RGB (Red-Green-Blue, i.e., color image) cameras to capture surgical procedures and to detect patient entrance/exiting events. However, gathering videos and/or images from the OR is subject to various privacy rules or concerns because of the captured images include multitudes of personal identifiable information (PII). As such, operating RGB cameras in the OR not only requires patient's consent but it is crucial to have the PII removed from the video data (also referred to as "video data de-identification" or "OR video de-identification") before using the captured images, which inevitably add to the cost and complexity of color-camera-based solutions. Note that under normal circumstances, standard RGB video images include sufficient information for detecting each person and subsequently de-identifying faces or bodies inside the images. However, personnel inside an OR are usually wearing Personal Protective Equipments (PPEs) including face masks, face shields, glasses, goggles, caps, gowns, etc. As a result, standard RGB video images are oftentimes unreliable for detecting human features (in particular facial features), and therefore insufficient for OR personnel detection, tracking and de-identification purposes. The above challenges to OR personnel detection and tracking are exacerbated under low lighting conditions, e.g., during a surgery when the OR lights are turned off and the surgical lights are turned on.

Hence, what is needed is a video-based OR workflow management technique that can simultaneously perform OR objects and personnel tracking and OR video de-identification without the drawbacks of the existing techniques.

SUMMARY

Disclosed are various operating room (OR) personnel detection/de-identification and tracking systems and techniques based on three-dimensional (3D) geometric information embedded in depth images captured by a depth camera. Depth sensors or depth cameras are imaging devices that produce two-dimensional (2D) images by casting lights (typically in infrared wavelengths) and measuring distances of points in a scene based on the travel time or intensity of the reflected light. From the 2D distance images (also referred to as "depth images"), the three-dimensional (3D) geometry of the scene can then be generated. Note that most of the ORs only have RGB (red-green-blue, i.e., color) cameras installed for monitoring the OR workflow. OR videos captured by RGB/color cameras can provide visual feedback from the events taking place inside the OR, and analyzing and mining these OR videos can lead to improved OR efficiency. However, the images or videos collected in an OR need to be de-identified to remove all personally identifiable information (PII) prior to performing OR video analysis and storage. Note that to remove the PII from the OR videos, the OR PII such as personnel's faces may need to be identified first. Unfortunately, RGB video images are generally unreliable and insufficient for OR personnel detection/de-identification purposes.

The depth images from a depth camera (such as in an RGB-D camera) can provide additional information not available in the color images from the RGB camera to identify OR personnel. This additional information can then be used to detect and track people in the 3D space in the OR even when people are heavily covered with Personal Protective Equipments (PPEs) or under poor lighting conditions. Specifically, the depth images can be used to generate 3D body shapes/contours for the detected OR personnel. Moreover, when leveraging machine-learning (ML) techniques, the depth images can also be used to identify a set of body joints/keypoints, and then construct a skeleton figure for each detected person. Next, both the detected 3D body shapes/contours of the identified person and estimated body joints can be inversely projected onto corresponding color images in the RGB video, thereby identifying not only the locations and outlines of the same person but the locations of the person's joints in the color images. Each identified person in the color images can then be blurred out, either to the entire body or just to portions of body containing the PII, thereby de-identifying the detected person in the color images. Moreover, the identified skeleton figure of a detected person can be used to infer an action of the detected person in the color images.

In addition to being used to detect/de-identify OR personnel in color images, the depth images and depth cameras can also be used to identify and/or track certain target objects (including but not limited to: a patient bed and a surgical table) in the OR during a surgery, which is another aspect of the overall OR workflow monitoring and management. Hence, this disclosure also provides an OR workflow tracking system which is designed to identify and/or track target objects, such as patient beds and surgical tables based on geometric features of the target objects. The proposed OR workflow tracking system again leverages a depth camera's ability to resolve 3D geometries in the monitored environment and the shapes of the target objects in the environment. Based on the geometric properties such as 3D dimensions and surface orientations that can be extracted from depth images, the proposed OR workflow tracking system can identify a mobile patient bed from the captured depth images, and then track the movement of the identified patient bed through a sequence of depth images. Moreover, the proposed OR workflow tracking system can detect events when a patient bed entering or exiting an OR, and thus can enable automatic notification of such events, thereby improving OR efficiency. Compared with conventional color-camera-based techniques, the depth-image-based workflow tracking techniques provide significantly high privacy protections.

In one aspect, a process for identifying and tracking a target object in an operating room (OR) is disclosed. This process may begin by receiving a depth image among a sequence of depth images captured by a depth camera installed in the OR. The process then generates a three-dimensional (3D) point cloud based on the depth image. Next, the process identifies a set of potential target points in the 3D point cloud that potentially belongs to the target object based on one or more target object criteria. The process next extracts one or more object clusters of 3D points from the set of potential target points using a data-point clustering technique. The process subsequently identifies the target object from the extracted one or more object clusters.

In some embodiments, the process generates the 3D point cloud based on the received depth image by projecting each 2D pixel (u, v) and the corresponding distance value d(u, v) in the depth image into a 3D point in a 3D-coordinate system aligned with the depth camera based at least on a known lens model of the depth camera.

In some embodiments, the process further includes the steps of, for each 3D point in the 3D point cloud: (1) computing a surface orientation at the 3D point based on one or more vector cross-products between two or more edges formed by the 3D point and two or more neighboring 3D points of the 3D point in the 3D point cloud; and (2) associating the computed surface orientation with the 3D coordinates of the 3D point.

In some embodiments, the process identifies the set of potential target points in the 3D point cloud that potentially belongs to the target object by: (1) transforming each 3D point and the associated surface orientation in the 3D point cloud into a 3D-coordinate system aligned with the ground surface of the OR; and (2) extracting the set of 3D potential target points from the transformed 3D point cloud by filtering the transformed 3D point cloud base on one or more geometrical criteria of the target object.

In some embodiments, the target object is a patient bed or a surgical table in the OR, and the process filters the transformed 3D point cloud base on the one or more geometrical criteria of the target object by: (1) filtering the transformed 3D point cloud based on a height of the patient bed or the surgical table by selecting a first subset of 3D points within the transformed 3D point cloud having height values within a range around the height of the patient bed or the surgical table; and (2) further filtering the subset of 3D points to obtain the set of potential target points by selecting a second subset of 3D points within the first subset of 3D points having associated surface orientations substantially perpendicular to the ground surface.

In some embodiments, the data-point clustering technique is a Density-Based Spatial Clustering of Applications with Noise (DBSCAN) clustering technique which is configured to identify a cluster of target points in the set of potential target points having a higher density than the remainder of the set of potential target points.

In some embodiments, the process identifies the target object from the extracted one or more object clusters by: for each object cluster in the extracted one or more object clusters: (1) generating a minimum bounding box for the object cluster; and (2) determining whether the object cluster is the target object by comparing the dimensions of the generated minimum bounding box against the dimensions of the target object.

In some embodiments, the process determines whether the object cluster is the target object by further applying one or more of the following detection requirements: (1) determining whether the number of data points inside the generated minimum bounding box satisfies a number-of-points requirement of the target object; (2) determining whether the orientation of the generated minimum bounding box satisfies a surface orientation requirement of the target object; and (3) determining whether the position of the generated minimum bounding box satisfies a position requirement of the target object.

In some embodiments, after installing the depth camera but prior to generating the 3D point cloud, the process also calibrates the depth camera to obtain the position and the orientation of the depth camera with respect to a ground surface in the OR.

In some embodiments, after identifying the target object from the extracted one or more object clusters, the process further includes tracking the identified target object by determining if the identified target object has been previously-identified in one or more preceding depth images in the sequence of depth images. If so, the process subsequently estimates a movement of the identified target object. Otherwise, the process determines that the identified target object is a newly-identified target object not previously identified.

In some embodiments, the identified target object includes a patient bed inside the OR. Note that by tracking the identified patient bed in the OR, the process is able to detect the following OR workflow events associated with a patient during a surgical procedure: (1) a patient entering the OR event; (2) a patient entered the OR event; (3) a patient exiting the OR event; and (4) a patient exited the OR event.

In some embodiments, using the depth camera and the sequence of depth images to track the identified target object in the OR eliminates privacy issues generally associated with recorded OR videos.

In another aspect, a system for identifying and tracking a target object in an OR is disclosed. This system includes: a depth camera installed in the OR; one or more processors coupled to the depth camera; and a memory coupled to the one or more processors. Moreover, the memory stores instructions that, when executed by the one or more processors, cause the system to: (1) receive a depth image among a sequence of depth images captured by the depth camera; (2) generate a 3D point cloud based on the depth image; (3) identify a set of potential target points in the 3D point cloud that potentially belongs to the target object based on one or more target object criteria; (4) extract one or more object clusters from the set of potential target points using a data-point clustering technique; and (5) identify the target object from the extracted one or more object clusters.

In some embodiments, the memory further stores instructions that, when executed by the one or more processors, cause the system to track the identified target object in the OR through the sequence of depth images.

BRIEF DESCRIPTION OF THE DRAWINGS

This patent or application file contains at least one drawing executed in color. Copies of this patent or patent application publication with color drawings will be provided by the Office upon request and payment of the necessary fee.

The structure and operation of the present disclosure will be understood from a review of the following detailed description and the accompanying drawings in which like reference numerals refer to like parts and in which.

DETAILED DESCRIPTION

Figure 1:
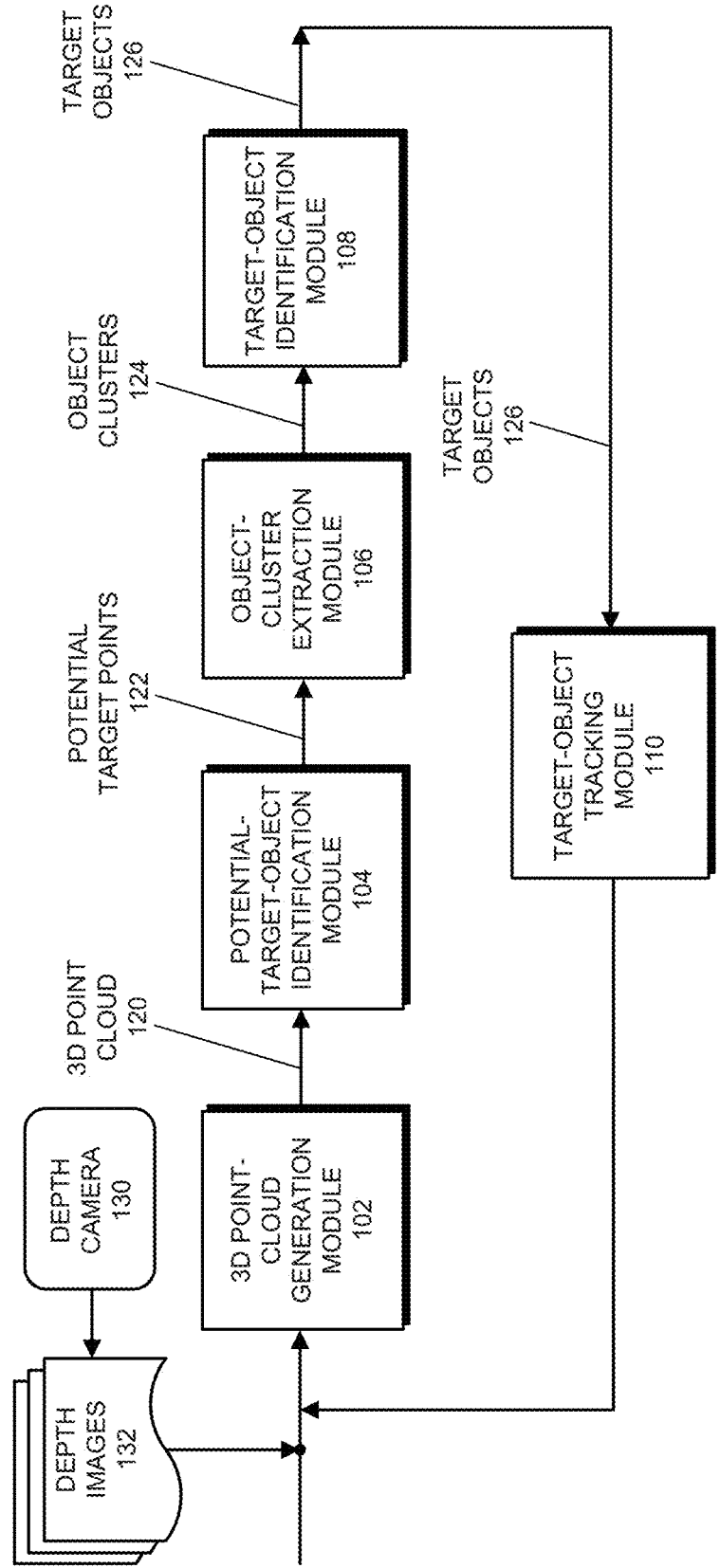
FIG. 1 illustrates a block diagram of the disclosed operating room (OR) target-object detection and tracking system for identifying one or more target objects and tracking each identified target object during a surgery in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Terminology

Throughout this patent disclosure, the terms "RGB camera," "two-dimensional (2D) RGB camera," and "color camera" are used interchangeably to mean a digital imaging sensor/camera capable of capturing 2D color images of persons and objects. Moreover, the term "three-dimensional (3D) depth camera" and "depth camera" are used interchangeably to mean a range imaging device capable of producing 2D images containing distance information on image pixels to surfaces in a scene. Furthermore, the term "patient bed" is used to refer to a mobile bed or a stretcher on which a patient is transported into/out of an operating room (OR); whereas the term "surgical table" is used to refer to a stationary table in the OR on which a patient lies during a surgical procedure.

Overview

Disclosed are various operating room (OR) personnel detection/de-identification and tracking systems and techniques based on three-dimensional (3D) geometric information embedded in depth images captured by a depth camera. Depth sensors or depth cameras are imaging devices that produce two-dimensional (2D) images by casting lights (typically in infrared wavelengths) and measuring distances of points in a scene based on the travel time (i.e., time-of-flight) or intensity of the reflected light. From the 2D distance images (also referred to as "depth images"), the three-dimensional (3D) geometry of the scene can then be generated. Some commercially available depth cameras include the Azure Kinect™ Camera from Microsoft, the RealSense™ LiDAR Camera from Intel, etc. Note that both of these cameras are RGB-D (i.e., red-green-blue and depth) cameras, which means they not only include a depth camera that captures depth images, but a color camera that captures regular color video images.

Note that most of the ORs in hospitals generally only have RGB cameras installed for monitoring the OR workflow. OR videos captured by these cameras can provide visual feedback from the events taking place inside the OR, and analyzing and mining these OR videos can lead to improved OR efficiency. However, given various data collection protocols and privacy regulation or rules in an OR, the images or videos collected in an OR need to be de-identified to remove all personally identifiable information (PII) of both the patients and OR personnel prior to performing OR video analysis and storage. Note that to remove the OR PII such as personnel's faces from the OR videos, the OR PII often needs to be identified first. Unfortunately, as discussed in the background section, RGB video images face a great deal of challenges for OR personnel detection, and therefore are often unreliable and insufficient for detection/de-identification purposes.

When an OR also has a depth camera installed, either in the form of an RGB-D camera or as a standalone depth camera next to an RGB camera, the depth images from the depth camera can provide additional information not available in the color images from the RGB camera to identify OR personnel. This additional information can then be used to detect and track people in the 3D space in the OR even when people are heavily covered with Personal Protective Equipments (PPEs) or under poor lighting conditions. Specifically, the depth images can be used to generate 3D body shapes/contours for the detected OR personnel. Moreover, when leveraging machine-learning (ML) techniques, the depth images can also be used to identify a set of body joints, and then construct a skeleton figure for each detected person. Next, both the detected 3D body shapes/contours of the identified person and estimated body joints can be inversely projected onto corresponding color images in the RGB video, thereby identifying not only the locations and outlines the same person but the locations of the person's joints in the color images. Each identified person in the color images can then be blurred out, either to the entire body or just portions of body containing the PII, thereby de-identifying the detected person in the color images. Moreover, the identified skeleton figure of a detected person can be used to infer an action of the detected person in the color images.

In addition to being used to detect/de-identify OR personnel in color images, the depth images and depth cameras can also be used to identify and/or track certain target objects (including but not limited to: a patient bed and a surgical table) in the OR during a surgery, which is another aspect of the overall OR workflow monitoring and management. Hence, this disclosure also provides an OR workflow tracking system which is designed to identify and/or track target objects, such as patient beds and surgical tables based on geometric features of the target objects. The proposed OR workflow tracking system again leverages a depth camera's ability to resolve 3D geometries in the monitored environment and the shapes of the target objects in the environment. Based on the geometric properties such as 3D dimensions and surface orientations that can be extracted from depth images, the proposed OR workflow tracking system can identify a mobile patient bed from the captured depth images, and then track the movement of the identified patient bed through a sequence of depth images. Moreover, the proposed OR workflow tracking system can detect events when a patient bed entering or exiting an OR, and thus can enable automatic notification of such events, thereby improving OR efficiency. Compared with conventional color-camera-based techniques, the depth-image-based workflow tracking techniques provide significantly high privacy protections.

Depth-Image-Based Operating Room (OR) Object Detection and System

FIG. 1 illustrates a block diagram of a disclosed operating room (OR) target-object detection and tracking system 100 (or "OR tracking system 100") for identifying one or more target objects and tracking each identified target object during a surgery in accordance with some embodiments described herein. As can be seen in FIG. 1, OR tracking system 100 can include at least the following processing modules: (1) 3D point-cloud generation module 102; (2) potential-target-object identification module 104; (3) object-cluster extraction module 106; (4) target-object identification module 108; and (5) target-object tracking module 110, which are coupled to each other to form a processing loop. Note that the disclosed target-object identification and tracking operations of OR tracking system 100 can begin when 3D point-cloud generation module 102 receives a sequence of raw depth images 132, one image at a time, from depth camera 130 installed in the OR. Depth camera 130 can include a time-of-flight (ToF) sensor using an infrared light source. In other embodiments, depth camera 130 can include a LiDAR (Light Detection And Ranging) sensor. Note that depth camera 130 can be but not necessarily a part of OR tracking system 100. Moreover, depth camera 130 can be a part of an integrated RGB-D camera.

Note that after setting up depth camera 130 in the OR, it is necessary to obtain the lens model of depth camera 130 as well as the position and orientation of the depth camera 130 with respect to the ground surface in the OR. The lens model of depth camera 130 can be obtained by a depth-camera calibration process, wherein the lens model is typically provided by the manufacturer. In some embodiments, the pose (i.e., the position and orientation) of depth camera 130 relative to the ground surface can be obtained based on the captured depth images 132. Specifically, after depth camera 130 is installed and fixed in place in the OR, new depth images 132 can be captured and the ground surface in the images can then be identified. In some embodiments, the ground surface in the new depth images 132 can be chosen manually from a selection of surfaces extracted from the depth image using the random sample consensus (RANSAC) technique. After identifying the ground surface points, the 3D coordinates of the identified ground surface points can be used to determine the pose of depth camera 130 through any known camera pose-estimation technique. Note that the pose of depth camera 130 can also be directly determined if depth camera 130 is equipped with an inertial measurement unit (IMU) that can automatically measure the orientation of depth camera 130 relative to gravity. In some embodiments, the above-described camera-pose calibration process can be implemented on 3D point-cloud generation module 102. In other embodiments, the camera-pose calibration process can be implemented on a separate processing module before 3D point-cloud generation module 102 (not explicitly shown in FIG. 1).

After calibrating depth camera 130 using depth images 132, 3D point-cloud generation module 102 is configured to receive a new/unprocessed depth image 132 in the sequence of depth images 132 captured in the OR as input and generate a corresponding 3D point cloud 120 as output. More specifically, 3D point cloud 120 can be obtained by projecting each 2D pixel (u, v) and the corresponding measured depth/distance value d(u, v) in the received 2D depth image 132 into a 3D point in a 3D-coordinate system (x, y, z) aligned with depth camera 130 using the known lens model of depth camera 130. Note that each point in 3D point cloud 120 represents a 3D position on a surface of an object in the OR from where the light cast by depth camera 130 reflects after hitting the surface of the object. A person skilled in the art will appreciate that, once the 3D point cloud 120 is constructed, the orientation of the object surface at a given 3D position in 3D point cloud 120 can be determined by a surface normal vector (or simply "surface normal")

calculated from the vector cross-product of two edges formed by the given 3D position with two neighboring 3D positions.

In some embodiments, a more accurate surface orientation value at a given 3D point can be obtained by using a 4-point computation scheme. In this scheme, given a 3D position, four additional 3D positions in the 3D point cloud 120 are identified which include: (1) a first 3D position located above the given 3D point; (2) a second 3D position located below the given 3D point; (3) a third 3D position located to the left of the given 3D point; and (4) a fourth 3D position located to the right of the given 3D point. Note that by combining the original 3D position with the four additional 3D positions, at least four surface normal values can be computed. Hence, the more accurate surface orientation for the given 3D point can be obtained by computing the average of the four surface normal values.

As can be seen in FIG. 1, 3D point cloud 120 and the computed surface orientations are received by potential-target-object identification module 104, which is configured to identify those 3D positions potentially belong to the target object (also referred to as "potential target points" below), such as a mobile patient bed (or simply a "patient bed") or a stationary surgical table (or simply a "surgical table"), and subsequently output a set of potential target points 122. Without losing generality, it is assumed that the target object in the OR being detected has a regular geometry and at least one surface that is parallel to the ground surface (i.e., in a horizontal plane) of the OR.

In some embodiments, prior to identifying the potential target points 122, potential-target-object identification module 104 is first configured to transform each 3D position in 3D point cloud 120 and the associated surface orientation of the 3D position into a new coordinate system based on the ground surface in the OR. This is because certain target object to be detected in the OR, such as the patient beds can be specified in the same reference frame as the ground surface in the OR. After the coordinate transformation, potential-target-object identification module 104 is further configured to extract a first set of potential target points in the transformed 3D point cloud that have height values close to a predetermined height of the target object. Note that the first set of potential target points do not have to have the exact height of the target object. Instead, the first set of potential target points can include those 3D points in the 3D point cloud 120 that have height values within a predetermined range around the height value of the target object (e.g., a range of height values centered approximately around the height of the target object). Note that obtaining the first set of potential target points can be considered as filtering the 3D point cloud 120 with an object-height filter. After obtaining the first set of potential target points, potential-target-object identification module 104 is further configured to extract the set of potential target points 122 by filtering the first set of potential target points based on a surface orientation requirement (i.e., a surface-orientation filter) of the target object, such as the patient bed or the surgical table. Specifically, the second filtering step of potential-target-object identification module 104 will obtain the set of potential target points 122 for the target object by extracting from the first set of potential target points, a subset of the target points that have the associated surface orientations substantially equal to the target surface orientation (e.g., an orientation perpendicular to the ground surface when the target object is the patient bed or the surgical table).

Figure 2A:
FIG. 2A represents the filtered result after applying an object-height filter to the established 3D point cloud in an exemplary process of extracting potential target points belonging to a patient bed in an OR in accordance with some embodiments described herein.
Figure 2B:
FIG. 2B represents the filtered result after applying a surface-normal filter to the established 3D point cloud in the exemplary process of extracting potential target points belonging to the patient bed in accordance with some embodiments described herein.
Figure 2C:
FIG. 2C represents the combined filtered result of the object-height filter in FIG. 2A and the surface-normal filter in FIG. 2B in the exemplary process of extracting potential target points belonging to the patient bed in accordance with some embodiments described herein.

FIGS. 2A-2C illustrates an exemplary process of extracting potential target points belonging to a patient bed (i.e., the target object) in the OR from an established 3D point cloud generated based on a single frame of depth image in accordance with some embodiments described herein. Note that in each of the FIGS. 2A-2C, the lime color is used to represent extracted/filtered target points. Specifically, FIG. 2A represents the filtered result after applying an object-height filter to the established 3D point cloud in accordance with some embodiments described herein. As can be seen in FIG. 2A, the extracted target points (in the lime color) after applying the height filter include all 3D points (both objects and people) in the established 3D point cloud that satisfy the height requirements for the patient bed. FIG. 2B represents the filtered result after applying a surface-normal filter to the established 3D point cloud in accordance with some embodiments described herein. As can be seen in FIG. 2B, the extracted target points (also in the lime color) after applying the surface-normal filter include all 3D points (including, objects, people, and ground) that satisfy the surface-normal requirements for the patient bed. FIG. 2C represents the combined filtered result of the object-height filter in FIG. 2A and the surface-normal filter in FIG. 2B in accordance with some embodiments described herein. As can be seen in FIG. 2C, the resulting extracted target points (also in the lime color) after combining the filtered results of both the height filter and the surface-normal filter include only those extracted target points that satisfy both the height requirements and the surface-normal requirements for the patient bed (i.e., the intersection of FIG. 2A and FIG. 2B). As a result, those potential target points belong to a patient bed 202 located somewhere in the middle of the depth image can be visually and exclusively identified.

Returning to FIG. 1, note that after extracting the set of potential target points 122 based on the height and surface normal requirements of the target object, object-cluster extraction module 106 is applied to the set of potential target points 122 to extract one or more object clusters 124 from the set of potential target points 122. Note that each extracted object cluster is a cluster of 3D points in the 3D point cloud 120 that has a high likelihood being the target object (e.g., a patient bed or a surgical table). In some embodiments, object-cluster extraction module 106 is configured to identify each object cluster 124 in the set of potential target points 122 using a data-point clustering technique. In some embodiments, the data-point clustering technique is a "Density-Based Spatial Clustering of Applications with Noise" (DBSCAN) clustering technique which is configured to identify a 3D volume formed by a subset of 3D points in the set of potential target points 122, wherein the 3D volume has a higher density than the remainder of the set of potential target points 122. In addition to using DBSCAN clustering technique, other types of clustering techniques may also be used to identify one or more object clusters 124 from the extracted set of potential target points 122, wherein different clustering techniques can have varying performances depending on the characteristics of the 3D depth image data. However, regardless of the clustering technique used by object-cluster extraction module 106, the output of object-cluster extraction module 106 includes one or more 3D volumes/clusters 124 that potentially represent one or more target objects, e.g., both a patient bed and a surgical table in the OR.

Note that a potential problem that can occur when identifying potential target objects from the depth images using the above-described data clustering technique is that, when the target object becomes obstructed by another object in the OR, e.g., an OR personnel standing in front of a patient bed or a surgical table, the data clustering technique functions to divide the target object into two object clusters, i.e., two separate objects. In some embodiments, the above problem caused by target object partial-occlusion can be alleviated by storing the original depth image containing the unobstructed target object in a memory when the target object was initially identified and extracted. The stored depth image containing the target object can then be propagated as OR de-identification system 100 continues to process the sequence of depth images 132. In some embodiments, before processing a new depth image, the new depth image can be compared against the stored depth image. Because the location of the target object in the new depth image is known (assuming that the target object has not moved), target object obstruction in the new depth image by another object can be detected when a portion of the new depth image is found to have smaller depth or distance values than the stored depth image where the target object is location. When the target object obstruction is detected in the new depth image, those target points in the current depth image found to be obstructed can be replaced/added in with the corresponding unobstructed portion of the stored depth image.

Referring back to FIG. 1, after the one or more object clusters 124 have been extracted, target-object identification module 108 in OR tracking system 100 can be used to positively identify one or more target objects (e.g., one or more patient beds and/or one or more surgical tables) 126 from the one or more object clusters 124. To do so, target-object identification module 108 can first receive a list of target object descriptions, wherein the list of target object descriptions include geometrical properties, including but not limited to sizes, dimensions, orientations, positions for each of the one or more target objects to be identified. Target-object identification module 108 is further configured to create a minimum bounding box for each object cluster in the identified one or more object clusters 124. Next, target-object identification module 108 is configured to determine whether the cluster of 3D points within a given bounding box belongs to a target object (e.g., a patient bed or a surgical table) by comparing the dimensions (e.g., the length and width) of the given bounding box to the dimensions of the target object, e.g., the length and width of a surgical table specified in the list of target object descriptions. Hence, target-object identification module 108 can output an identified target object 126 if the dimensions of the given bounding box match the dimensions of the target object.

In some embodiments, in addition to applying the dimension criteria, target-object identification module 108 can apply additional detection criteria to an object cluster and the corresponding bounding box to determine whether the object cluster 124 is a target object with an even higher confidence level. These additional detection requirements can include a point criterion: i.e., if the number of 3D points inside the created bounding box satisfies the number of point of the target object. In some embodiments, the additional detection criteria can also include determining whether the position and orientation of the generated bounding box match the position and orientation the target object specified in the list of target object descriptions. For example, a surgical table will have a horizontal orientation and its position is typically near the center of the OR.

While various functional modules, techniques, and processes are described to identify one or more target object 126 from a single frame of depth image 132, OR tracking system 100 is configured with a loop structure which continuously receives and processes the sequence of depth images 132, one depth image at a time, using the various functional modules and the object detection/identification techniques described above. As a result, OR tracking system 100 can generate a sequence of positions, orientations, and corresponding bounding boxes for each identified target object 126 in the OR. As can be seen in FIG. 1, OR tracking system 100 further includes target-object tracking module 110 configured to continuously identify and therefore track the same identified target object 126 through the sequence of depth images 132 based on the corresponding sequence of positions, orientations, and bounding boxes. In various embodiments, the received depth images 132 are real-time depth images captured in the OR, and OR tracking system 100 is configured to continuously identify and track a given target object 126 in real time.

In some embodiments, target-object tracking module 110 tracks each identified target object in consecutive depth images based on statistical similarities. Specifically, for a previously-identified target object in the previous/earlier depth image in a given pair of consecutive depth images, target-object tracking module 110 subsequently performs statistical analysis on a set of determined object features (e.g., the bounding box dimensions, position, and orientation) of a newly-identified target object within the current/later depth image in the given pair of consecutive depth images against a corresponding set of determined object features for the previously-identified target object. Hence, the statistical analysis generates a set of similarity values for the newly-identified target object. If the computed similarity values are sufficiently high, the newly-identified target object can be determined to be the same object as the previously-identified target object in the previous/earlier depth image. However, if a newly-identified target object in the current depth image has no determined object feature that is sufficiently close to any of the previously-identified target objects in the previous depth image, the newly-identified target object in the current image can be reasonably determined to be a new target object not previously identified, such a new patient bed, or a re-identified target object after a previously-identified target object was later lost. Note that the above-described object tracking technique can reliably and consistently track the movement of each identified target object in the OR environment if the frame rate of depth camera 130 is sufficiently high (e.g., >30 frame-per-second (FPS)) so that the movement of a given target object does not produce a drastic positional change between consecutive depth-image frames.

Figure 3:
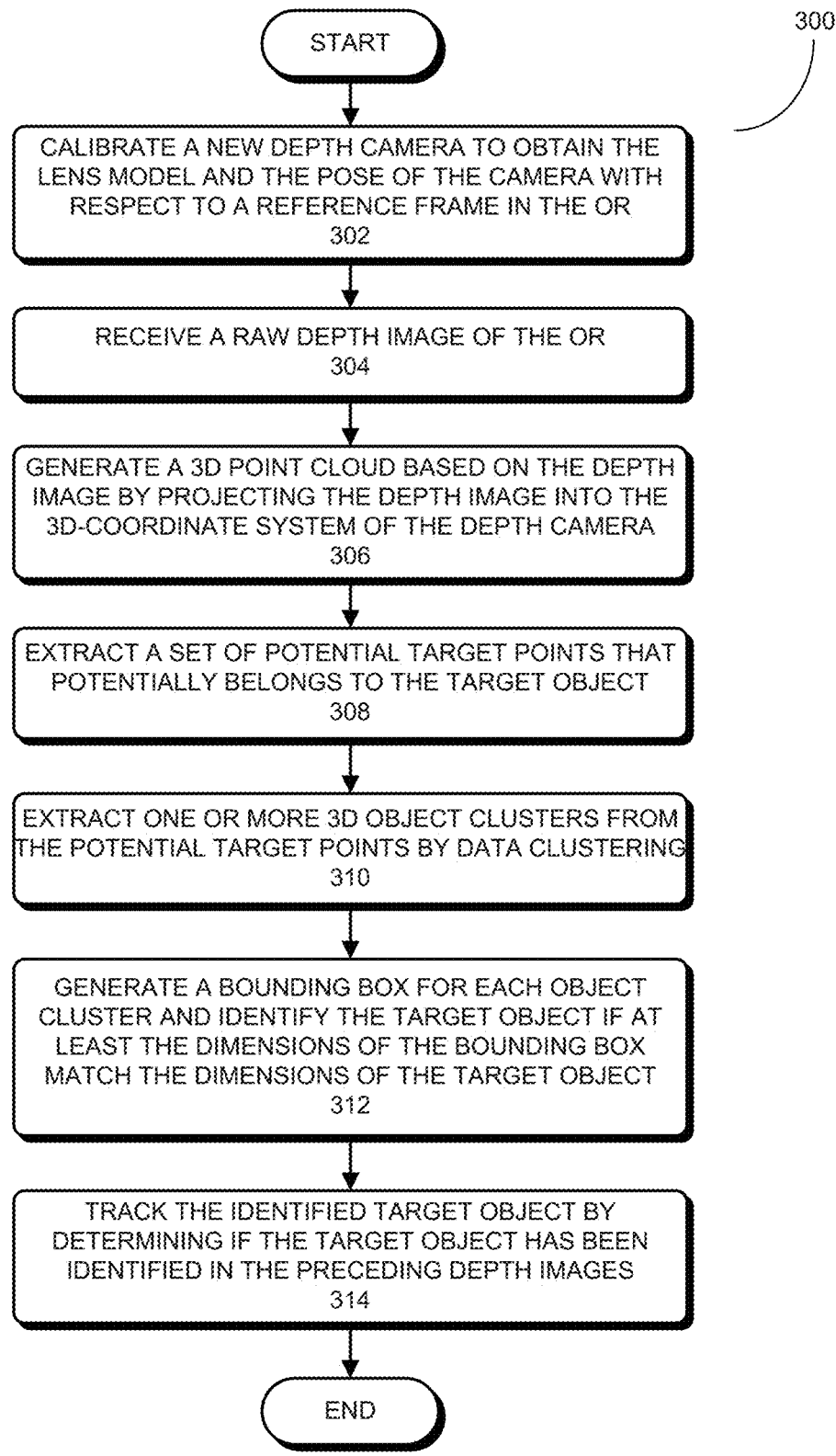
FIG. 3 presents a flowchart illustrating an exemplary process for automatically identification and tracking a target object in the OR based on a sequence of depth images captured by a depth camera in accordance with some embodiments described herein.

FIG. 3 presents a flowchart illustrating an exemplary process 300 for automatically identification and tracking a target object in the OR based on a sequence of depth images captured by a depth camera in accordance with some embodiments described herein. In one or more embodiments, one or more of the steps in FIG. 3 may be omitted, repeated, and/or performed in a different order. Accordingly, the specific arrangement of steps shown in FIG. 3 should not be construed as limiting the scope of the technique.

Process 300 may begin by calibrating a newly-installed depth camera to obtain the lens model and the pose of the depth camera with respect to a reference frame in the OR (step 302). In some embodiments, the pose (i.e., the position and orientation) of the newly-installed depth camera can be determined with respect to the ground surface (reference frame) in the OR using the depth images captured by the newly-installed depth camera. This is useful for detecting certain target objects in the OR, such as the patient beds and surgical tables that can be specified in the same reference frame as the ground surface in the OR. Process 300 next receives a raw depth image of the OR captured by the depth camera as an input (step 304). Note that the received raw depth image is a single frame of a depth-image video captured by the depth camera. In some embodiments, the depth-image video is a real-time video captured during a surgical procedure. Next, process 300 generates a 3D point cloud based on the raw depth image by projecting the 2D depth image into the 3D-coordinate system of the depth camera based on the lens model of the depth camera (step 306). Note that after constructing the 3D point cloud, a surface normal vector at each 3D point in the 3D point cloud can be computed and then associated with that 3D point.

Figure 4:
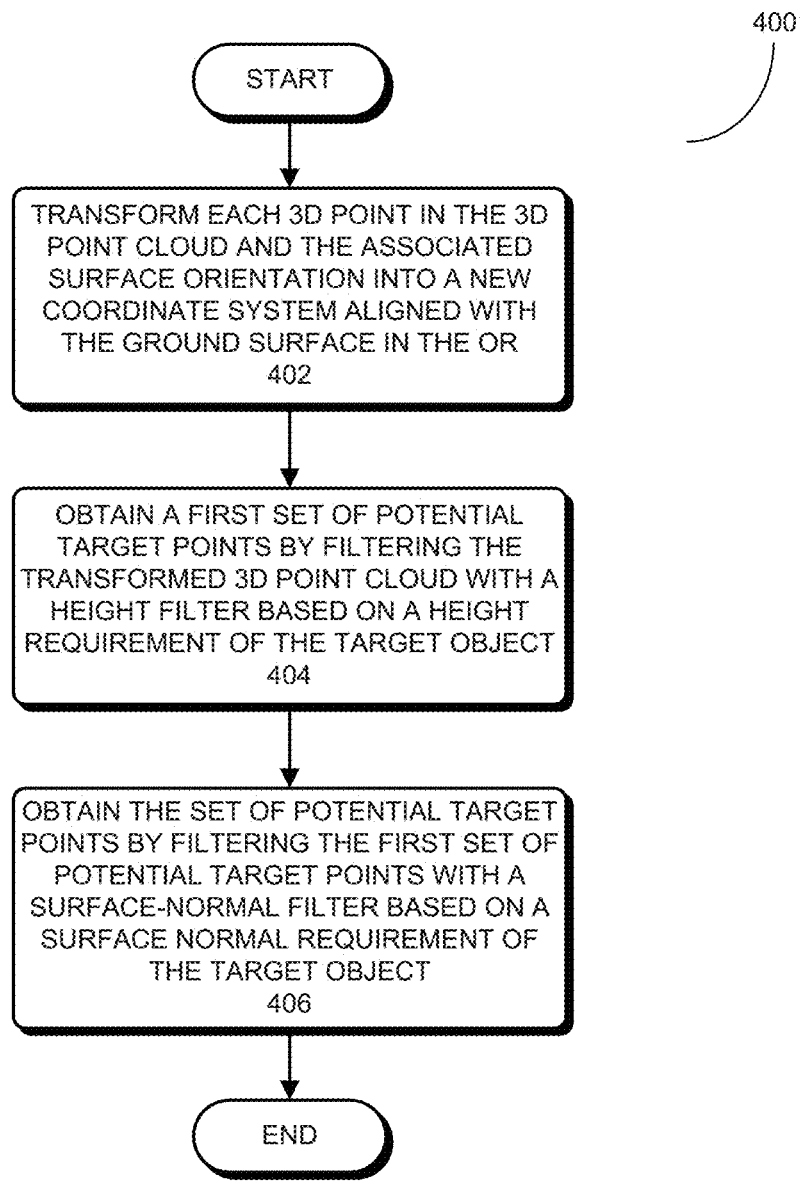
FIG. 4 presents a flowchart illustrating an exemplary process for extracting a set of potential target points that potentially belongs to the target object from the 3D point cloud in accordance with some embodiments described herein

Next, process 300 extracts a set of potential target points that potentially belongs to the target object from the 3D point cloud (step 308). Note that step 308 can itself include a number of steps. For example, FIG. 4 presents a flowchart illustrating an exemplary process 400 for extracting a set of potential target points that potentially belongs to the target object from the 3D point cloud in accordance with some embodiments described herein. In one or more embodiments, one or more of the steps in FIG. 4 may be omitted, repeated, and/or performed in a different order.

Process 400 can include transforming each 3D point in the 3D point cloud and the associated surface orientation into a new coordinate system aligned with the ground surface in the OR (step 402). This is because certain target object to be detected in the OR, such as the patient beds and surgical tables can be specified in the same reference frame as the ground surface in the OR. Next, process 400 obtains a first set of potential target points by filtering the transformed 3D point cloud with a height filter based on a height requirement of the target object (step 404). In some embodiments, each target point in the first set of potential target points has a height value within a predetermined range around the known height of the target object. Process 400 next obtains the set of potential target points by filtering the first set of potential target points with a surface-orientation filter based on a surface-normal requirement of the target object (step 406). For example, if the target object is a patient bed or a surgical table, the extracted set of potential target points would have surface normal values substantially equal to that of the ground surface of the OR. In some embodiments, the extracted set of potential target points can be stored for use at a later time in an object-occlusion/obstruction recovery process described above.

Returning to FIG. 3, after extracting the set of potential target points, process 300 next extracts one or more 3D object clusters from the set of potential target points using a data clustering technique, wherein each of the 3D object clusters has a high likelihood being the target object (step 310). As described above, the data-point clustering technique can be a DBSCAN-based clustering technique. Next, for each object cluster in the extracted one or more 3D object clusters, process 300 generates a minimum bounding box for the object cluster and identifies the object cluster as the target object if at least the dimensions of the generated minimum bounding box match the dimensions of the target object (step 312). In some embodiments, to increase the confidence of the identified target object, step 312 in process 300 can apply one or more additional detection requirements to the 3D object cluster that are listed below: (1) determining whether the number of data points inside the generated minimum bounding box matches the number-of-points requirement of the target object; (2) determining whether the orientation of the generated minimum bounding box matches the surface orientation requirement of the target object; and (3) determining whether the position of the generated minimum bounding box matches the position requirement of the target object.

After identifying the target object in the current depth image, process 300 can track the identified target object by determining if the same target object has been identified in the preceding or previous depth images (step 314). As described above, process 300 can perform a statistical image-feature analysis to compare the newly-identified target object against previously-identified target objects in the preceding or previous one or multiple depth image. If the newly-identified target object is determined to be the same as a previously-identified target object in one of the preceding or previous depth images, process 300 can estimate a movement (or lack of thereof) of the target object for object tracking and OR workflow monitoring purposes. Next, process 300 returns to step 304 to receive and process the next depth-image frame in a depth camera video, and the target-object identification process repeats while the target-object tracking process continues.

Target-Object Tracking for OR Workflow Management

Note that the ability of the disclosed OR tracking system 100 to continuously identify and track a target object in the OR during a surgery session can create multitudes of useful and novel OR management tools and applications for automated OR workflow monitoring and management. For example, one of the important applications of the disclosed OR tracking system 100 is to detect patients entering and exiting an OR by tracking patient beds. For this application, depth camera 130 can be installed next to the entrance/doorway of the OR. Moreover, a distance threshold can be defined relative to the entrance/doorway or another easily identifiable reference in the depth image for use to trigger an event detection. For example, the distance threshold to classify a detected target object as being an "inside object" or an "outside object" relative to the OR entrance can be measured with respect to a vertical centerline that evenly divides the image frame. This means that a detected object located to the left of the vertical centerline is considered as an outside object, whereas a detected object located to the right of the vertical centerline is considered as an inside object. Next, using the above-described target object identification and tracking techniques based on the captured depth images, events of patient beds entering or exiting the OR can be automatically detected each time such a target object is found to have passed the predefined distance threshold.

Figure 5A:
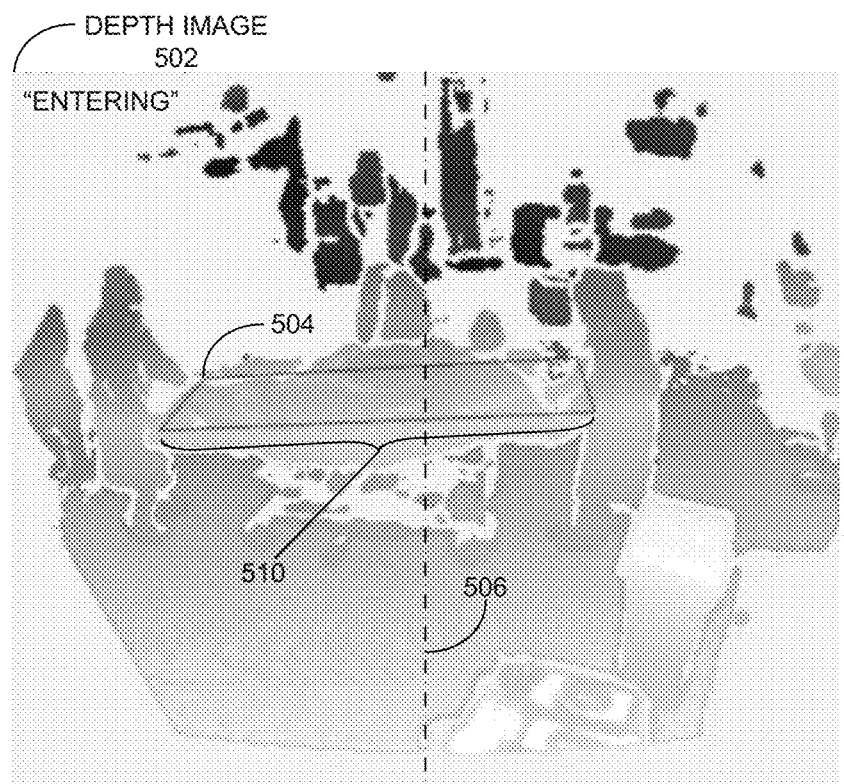
FIGS. 5A and 5B illustrate an exemplary process of detecting the event of a patient bed "entering the OR" by identifying and tracking a patient bed through a sequence of depth-image frames in accordance with some embodiments described herein.
Figure 5B:
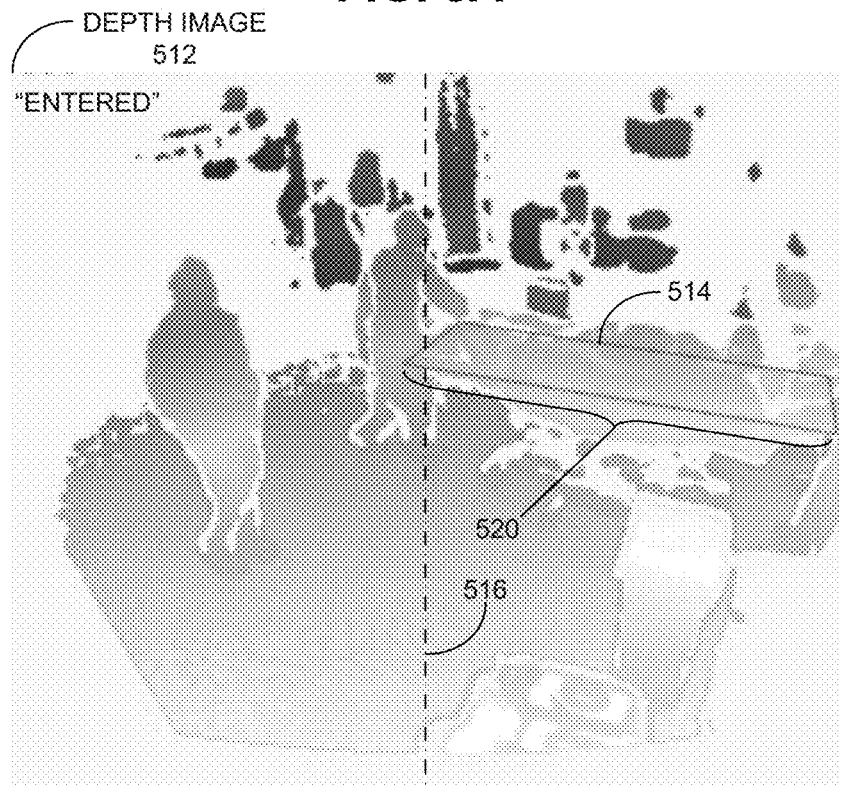

FIGS. 5A and 5B illustrate an exemplary process of detecting the event of a patient bed "entering the OR" by identifying and tracking a patient bed through a sequence of depth-image frames in accordance with some embodiments described herein. More specifically, FIG. 5A shows an identified patient bed 510 in a first depth image 502 which is marked with a top-view bounding box 504 and a vertical centerline 506 used as the distance threshold for the entering event detection. Hence, each object identified to the left of vertical centerline 506 is considered as an outside object, whereas an object located to the right of vertical centerline 506 is considered as an inside object. In depth image 502, patient bed 510 along with the corresponding bounding box 504 is shown to be more on the left side of the vertical centerline 506, i.e., on the entrance side of the OR. However, this information is insufficient to determine whether patient bed 510 is in the first state of "entering the OR" or the second state of "exiting the OR."

In some embodiments, the disclosed OR tracking system 100 can be further configured to determine a state for patient bed 510 based on the location change of bounding box 504 with respect to vertical centerline 506 in consecutive image frames. Specifically, OR tracking system 100 can be configured to track the four corners of bounding box 504 relative to the vertical centerline 506 and determine the state of patient bed 510 accordingly. Note that depth image 502 is among a sequence of depth images depicting the "entering the OR" event when patient bed 510 moves into the field of view from outside (i.e., from left side of depth image 502). The disclosed OR tracking system 100 can identify this event based on the number of corners in a sequence of generated bounding boxes of patient bed 510 initially changes from three or more corners on the left side of vertical centerline 506 to exactly two corners on each side of vertical centerline 506, as shown in FIG. 5A. As a result, depth image 502 can be classified as in the "Entering the OR" state, and designated with an "Entering" state label.

Note that as patient bed 510 continues to move further into the OR, the number of corners in the generated bounding boxes of the detected patient bed 510 in the sequence of processed depth images would change from two corners on each side of the vertical centerline to three or more corners on the right side of vertical centerline patient bed 510. For example, FIG. 5B shows an exemplary depth image 512 after depth image 502 that captures the above scenario. As can be seen in FIG. 5B, the identified patient bed 520 has a corresponding top-view bounding box 514 wherein three of the four corners of bounding box 514 are on the right side of a vertical centerline 516 used as the distance threshold in depth image 512. As a result, depth image 512 can be classified as in the "Entered the OR" state, and designated with an "Entered" state label.

Note that the above illustrated "Entering" and "Entered" labels/states can serve as real-time detection signals for the event of a new patient being wheeled into the OR and thus can enable automatic notification of such events. While we describe detecting the events/states associated with a patient bed "Entering the OR" and "Entered the OR," the same identifying and tracking process can be applied to another sequence of depth images to detect the events/states associated with a patient bed "Exiting the OR" and "Exited the OR." Similarly, the generated "Exiting" and "Exited" labels/states can serve as real-time detection signals of such an event which enable automatic and immediate notification when an existing patient exiting the OR, thereby improving OR efficiency. Note that the above-described depth-image-based techniques for identifying and tracking patients/patient beds entering/exiting the OR and other movements within the OR can not only avoid the above-described problems of interfering with the OR workflow associated with the tag or tracker-based solutions, but provide significantly higher privacy protections than RGB/color-camera-based solutions.

Depth-Image-Based OR Personnel Detection and De-Identification

As mentioned above, depth images from a 3D depth camera (such as the one within an RGB-D camera) can provide additional information not available in the color images from a 2D RGB camera to identify OR personnel. This additional information can then be used to detect and track people in the 3D space in the OR even when people are heavily covered with Personal Protective Equipments (PPEs) or under poor lighting conditions. Specifically, the depth images from the 3D depth camera can be used to generate 3D body shapes/contours for the detected OR personnel. Moreover, when leveraging machine-learning (ML) techniques, the depth images can also be used to identify a set of body joints/keypoints of each detected person, and to construct a skeleton figure/representation for each detected person. Next, both the generated 3D body shapes/contours of each detected person and the estimated body joints of the detected person from the depth images recorded by the 3D depth camera can be inversely projected onto corresponding 2D color images concurrently recorded by the RGB camera, thereby identifying not only the locations and outlines of the same person in the 2D color images but the locations of the person's joints in the 2D color images. Each identified person in the color images can then be blurred out, either to the entire body defined by the projected person's outline or just to portions of body containing the PII, e.g., the face and the torso with a possible name tag, thereby de-identifying the detected person in the 2D color images. Note that a fully de-identified color-image video using the disclosed de-identification technique can be recorded, displayed in real-time, played back at a later time, further processed, further analyzed, or uploaded to a cloud server. Moreover, the identified skeleton figure of a detected person can be used to infer an action of the detected person in the color images.

Figure 6:
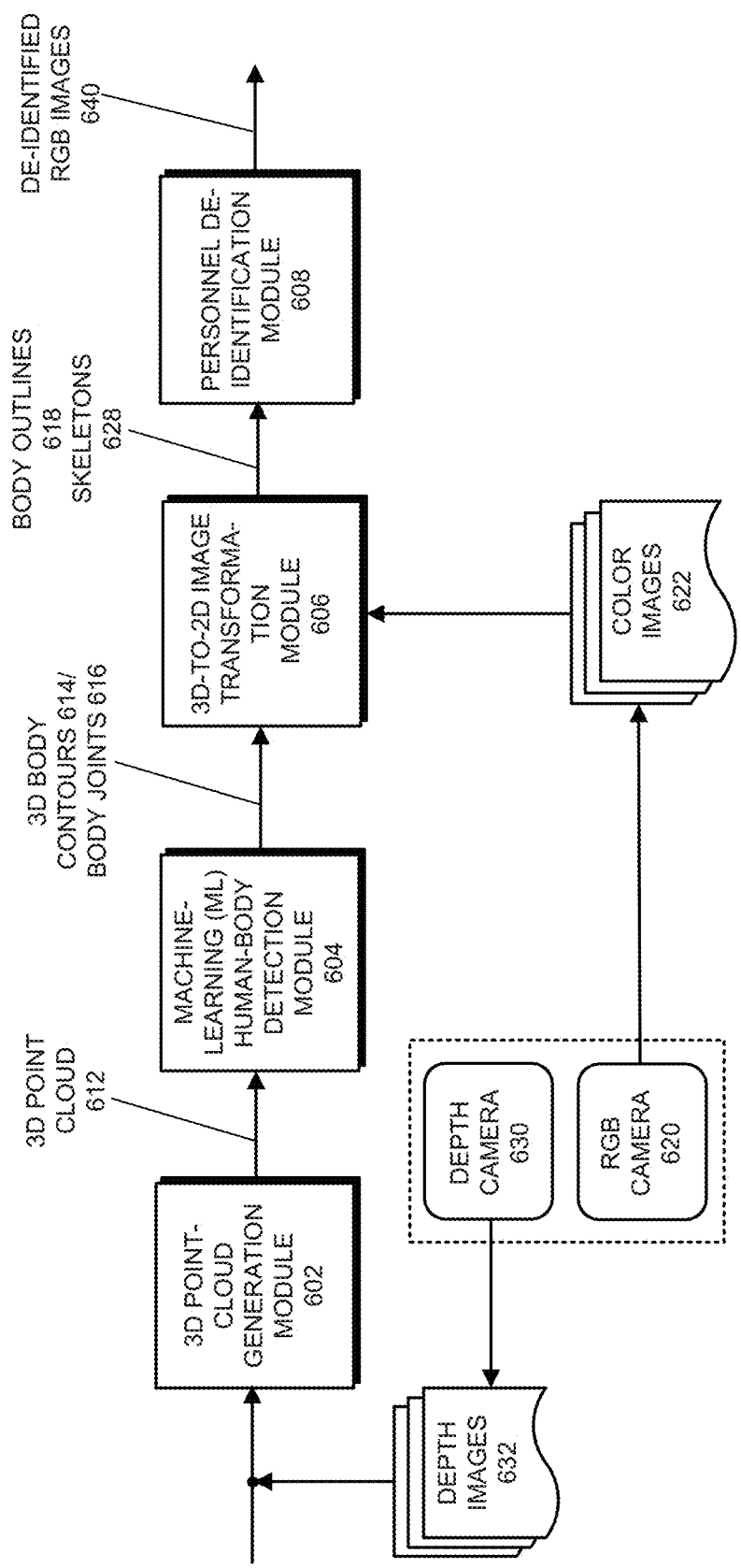
FIG. 6 illustrates a block diagram of a disclosed OR personnel de-identification system for de-identifying RGB/color images captured by an RGB camera installed in the OR in accordance with some embodiments described herein.

FIG. 6 illustrates a block diagram of a disclosed OR personnel de-identification system 600 (or "OR de-identification system 600") for de-identifying 2D RGB/color images captured by an RGB camera installed in the OR in accordance with some embodiments described herein. In the disclosed system 600 and the associated techniques, a 3D depth camera 630 (or simply the "depth camera 630") described above is installed in the OR in the vicinity of a 2D RGB camera 620 (or "RGB camera 620"). Note that RGB camera 620 can be a common OR monitoring camera or an OR security camera. Note that in an OR environment pertinent to this patent disclosure, there can be more than one RGB/color camera installed for the purposes of OR workflow/personnel tracking and/or OR security monitoring. In each of the above common use cases of RGB camera 620, PII of the OR personnel captured by RGB camera 620 needs to be removed. However, as discussed above, color images captured by RGB camera 620 are often unreliable and insufficient for detecting and de-identifying OR personnel captured in these color images.

The disclosed OR de-identification system 600 is designed to use the depth images captured by depth camera 630 to identify the 3D location, shape, contour, and different body joints/keypoints of each person in the OR and subsequently project the identified 3D shape/contour and estimated body joints of the detected person onto a corresponding 2D color/RGB image (or the "color image") captured by RGB camera 620. This projection simultaneously identifies and displays the outline of the detected person and the estimated locations of body joints of the detected person in the color image, thereby allowing the detected person to be de-identified in the color image. Note that depth camera 630 can include a time-of-flight (ToF) sensor that uses an infrared light source. In other embodiments, depth camera 630 can include a LiDAR sensor. In some embodiments, depth camera 630 and RGB camera 620 can be implemented as an integrated RGB-D camera. However, depth camera 630 and RGB camera 620 can also be implemented as separate cameras.

In the disclosed OR de-identification system 600, it is assumed that during a surgical procedure RGB camera 620 and depth camera 630 operate concurrently to capture the respective OR videos, i.e., color-image videos and depth-image videos. Hence, within any given time period during the surgical procedure, RGB camera 620 generates a sequence of color video images (or "color images") 622 and depth camera 630 generates a corresponding sequence of depth video images (or "depth images") 632. Moreover, at each given timestamp within the given time period during the surgical procedure, RGB camera 620 captures/generates an RGB video image (or "color image") 622 and depth camera 630 concurrently captures/generates a corresponding depth video image (or "depth image") 632. As such, the disclosed OR de-identification system 600 can simultaneously process the sequence of color images 622 and the sequence of depth images 632 in a pair-wire manner. In other words, OR de-identification system 600 is configured to process a given depth image 632 in the sequence of depth images 632 and use the extracted personnel information from the given depth image 632 to de-identify a corresponding color image 622 in the sequence of color images 622 that is captured at the same or substantially the same time as the given depth image 632. Hence, even though the disclosed OR de-identification system 600 is described below for a pair of color image 622 and depth image 632 captured at the same or substantially the same time, the disclosed system and technique can be repeatedly applied to a depth video and a corresponding RGB video in the frame-by-frame manner described below.

As can be seen in FIG. 6, OR de-identification system 600 includes a 3D point-cloud generation module 602 which receives a depth image 632 as input and generates a corresponding 3D point cloud 612 as output. Note that each point in 3D point cloud 612 represents a 3D location on the surface of an object or a person in the OR from where the light cast by depth camera 630 reflects after hitting the surface of the object/person. As mentioned above, 3D point-cloud generation module 602 is configured to project each 2D pixel (u, v) and the corresponding measured depth/distance value d(u, v) in the received 2D depth image 632 into a 3D point in a 3D-coordinate system (x, y, z) aligned with depth camera 630 using the known lens model of depth camera 630. Hence, in the obtained 3D point cloud 612, various 3D OR objects such as a patient bed, a surgical table and surgical equipments, and captured human such as the patient or the surgical staff, are represented by various 3D geometries formed by groups of 3D points in 3D point cloud 612.

After constructing 3D point cloud 612 from the given input depth image 632, various 3D geometries in 3D point cloud 612 that represent human bodies in the OR are identified. Specifically, OR de-identification system 600 uses a machine-learning-based (ML) human-body detection module 604 to receive and process 3D point cloud 612, and subsequently output a set of estimated 3D body contours 614 corresponding to the bodies of the detected people in the OR. In some embodiments, ML human-body detection module 604 can incorporate or operate in conjunction with the above-described data-point clustering technique to facilitate detecting human bodies in 3D point cloud 612. For example, ML human-body detection module 604 can first apply a data-point clustering technique (e.g., the DBSCAN clustering technique) to 3D point cloud 612 to identify a set of 3D-point clusters that potentially represent 3D objects including both non-human objects and OR personnel/humans. Next, ML human-body detection module 604 can use a ML human-body detection model to identify a subset of the set of 3D-point clusters that have high probabilities to represent human bodies. In various embodiments, this ML human-body detection model can be implemented using various known convolutional neural network (CNN/ConvNet) architectures. ML human-body detection module 604 can then extract a 3D body contour 614 from each identified 3D-point cluster in the subset of clusters by identifying those surface/boundary points/positions (also referred to as the "boundary surface") in the identified 3D-point cluster.

In addition to detecting and output 3D body contours 614, ML human-body detection module 604 is additionally configured to identify and output a set of body joints/keypoints 616 and corresponding probabilities for each identified body joint 616. In various embodiments, ML human-body detection module 604 can include a ML body-joint estimation model trained to estimate and identify a set of body joints based on each identified 3D-point cluster in the subset of clusters. More specifically, ML human-body detection module 604 can identify various body joints 616 from each identified 3D-point cluster in the subset of clusters by first extracting a set of shapes from the identified 3D-point cluster, and subsequently computing a set of orientations of the set of extracted shapes. ML human-body detection module 604 then estimates the set of body joints based on the set of extracted shapes and the set of computed orientations of the set of shapes. Note that the set of body joints 616 can include, but are not limited to the face, the neck, the chest, the shoulders, the elbows, the wrists, the fingers, the knees, the hip joints, and the ankles of the detected person. In some embodiments, ML human-body detection module 604 can additionally include a 3D pose-estimation model which is trained to estimate a pose of each detected person based on the spatial relationships of the set of estimated body joints 616. Note that each set of estimated body joints 616 can be used to construct a skeleton representation for the detected person in the given depth image 632.

Referring back to FIG. 6, after extracting the set of body contours 614 and the corresponding sets of estimated body joints 616 from 3D point cloud 612, OR de-identification system 600 next uses a 3D-to-2D image transformation module 606 to project/transform each extracted 3D body contour 614 in the set of body contours 614 into a 2D body outline 618 in the corresponding color image 622 representing the same detected person captured at the same or substantially the same time by RGB camera 620. Specifically, each set of 3D-coordinates of a given 3D point within the detected 3D body contour 614 is transformed from the 3D-coordinate system of 3D depth camera 630 to a pair of 2D-coordinates in the 2D-coordinate system of 2D RGB camera 620. Moreover, 3D-to-2D image transformation module 606 also projects/transforms each 3D position/body joint in the set of body joints 616 corresponding to a detected body contour 614 into a pair of 2D-coordinates in the 2D-coordinate system of RGB camera 620. Hence, the 3D-to-2D image transformation also obtains a corresponding skeleton figure (or simply "skeleton") 628 of the detected person in the corresponding color image 622. Note that both the transformed 2D body outline 618 and the corresponding skeleton FIG. 628 of a detected person from the depth image 632 can be directly overlaid onto the corresponding color image 622. Because a skeleton figure can be used to represent a detected person, OR de-identification system 600 can track the movement of each detected person based on a sequence of extracted skeleton FIG. 628 from a sequence of depth images 632 overlaid onto a corresponding sequence of color images 622.

Note that the above-described 3D-to-2D image transformation requires both a first calibrated lens model (i.e., a depth camera matrix) for depth camera 630 and a second calibrated lens model (i.e., an RGB camera matrix) for RGB camera 620. Hence, prior to performing the 3D-to-2D transformation, each of the depth camera 630 and RGB camera 620 are independently calibrated to obtain the first lens model for depth camera 630 and the second lens model for RGB camera 620. Note that even when depth camera 630 and RGB camera 620 are integrated within the same camera housing, they can still be slightly offset from each other, and therefore color images 622 captured by RGB camera 620 and depth images 632 captured by depth camera 630 have different reference frames. However, independently calibrating the depth camera and the RGB camera to obtain the respective lens models allows this offset to be corrected during the 3D-to-2D image transformation using 3D-to-2D image transformation module 606.

A know camera calibration technique to obtain a lens model can be found from https://docs.opencv.org/2.4/doc/tutorials/calib3d/camera_calibration/camera_calibration.html. Note that in a typically OR setup, depth camera 630 and RGB camera 620 are typically slightly offset from each other. This offset is factored into the transformation through the two lens models because each of the first and second lens models is constructed with respect to the respective reference frames of the respective cameras 620 and 630. After the transformation by 3D-to-2D image transformation module 606, a given 3D point representing a 3D position in point cloud 612 is projected to a pair of 2D coordinates in the RGB camera reference frame.

Further referring to FIG. 6, note that OR de-identification system 600 also includes a personnel de-identification module 608 following 3D-to-2D image transformation module 606. Personnel de-identification module 608 is configured to receive the color image 622 overlaid with the projected 2D body outlines 618 and the corresponding skeleton FIG. 628 and blur out or otherwise obfuscate the detected people/personnel in color image 622 based on the 2D body outlines 618 and/or skeleton FIG. 628. In some embodiments, personnel de-identification module 608 is configured to blur out or otherwise obfuscate the full bodies of the detected people/personnel by blurring out or otherwise obfuscating the portions of the color image 622 inside each of the overlaid 2D body outlines 618. As a result, personnel de-identification module 608 generates a de-identified RGB/color image 640 with fully-obfuscated OR personnel. In some other embodiments, personnel de-identification module 608 can also blur out or otherwise obfuscate the full bodies of the detected people/personnel based on the overlaid skeleton FIG. 628 without using 2D body outlines 618.

In some other embodiments, personnel de-identification module 608 is configured to selectively blur out only some portions of each detected person (instead of the full body) which are known to have PII or normally contain PII, such as the face of each detected person and upper torso of each detected person. To do so, for each detected person in the RGB image 622, personnel de-identification module 608 can combine the information of an overlaid 2D body outline 618 and the set of body keypoints in the corresponding skeleton FIG. 628 of the detected person to identify one or more portions of the body of the detected person, such as the face of the person or a portion the torso where a name tag is often attached to. Personnel de-identification module 608 next blurs out or otherwise obfuscates only those identified portions of the body of each detected person and generates a de-identified RGB image 640 that has each detected person sufficiently de-identified by blurred out the faces and other common types of PII.

Figure 7C:
FIG. 7C shows a de-identified RGB image of the original RGB image which has fully obfuscated both OR staff members based on the projected body outlines and/or skeleton figures in accordance with some embodiments described herein.
Figure 7B:
FIG. 7B shows a processed RGB image obtained by overlaying the unprocessed RGB image in FIG. 7A with the projected body outlines and skeleton figures extracted from a corresponding depth image captured by a 3D depth camera in accordance with some embodiments described herein.
Figure 7A:
FIG. 7A shows an exemplary unprocessed RGB image captured by a 2D RGB camera.

FIGS. 7A-7C illustrate an exemplary process and results of de-identifying OR personnel captured in 2D RGB/color images based on concurrently captured 3D depth images using the disclosed OR de-identification system and techniques in accordance with some embodiments described herein. Specifically, FIG. 7A shows an exemplary unprocessed RGB/color image 702 captured by a 2D RGB camera. Note that FIG. 7A includes two OR staff members: one facing the camera but having minimal visible facial features due to heavy facial covering; and the other facing the opposite direction against the camera and therefore with visible facial features. Note that the conventional face-detection/de-identification techniques based on image features of RGB image 702 would have difficulties to identify and subsequently de-identify the two staff members shown.

FIG. 7B shows a processed RGB image 704 obtained by overlaying RGB image 702 with the projected body outlines and skeleton FIGS. 706 and 708 comprising the corresponding sets of body joints extracted from a corresponding depth image in accordance with some embodiments described herein. Note that skeleton FIGS. 706 and 708 clearly identify the positions of the face/head of the two OR staff. Moreover, skeleton FIGS. 706 and 708 can be used to track the movement of each of the two OR staff through a sequence of RGB images. Finally, FIG. 7C shows a de-identified RGB image 710 of RGB image 702 which has fully obfuscated both OR staff members based on the projected body outlines and/or skeleton FIGS. 706 and 708 in accordance with some embodiments described herein.

Figure 8:
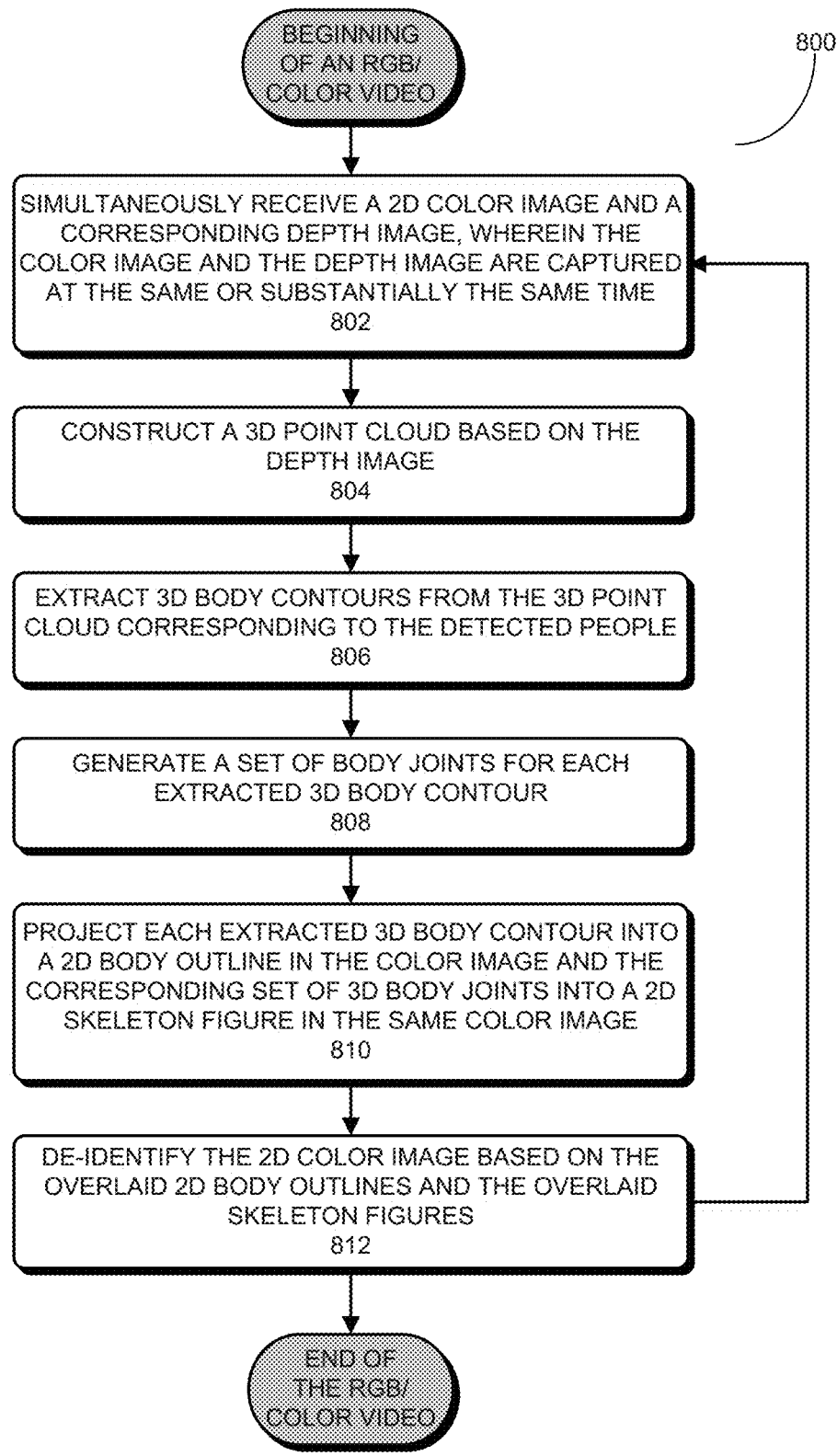
FIG. 8 presents a flowchart illustrating an exemplary process for de-identifying an RGB/color video captured by a 2D RGB camera installed in the OR in accordance with some embodiments described herein.

FIG. 8 presents a flowchart illustrating an exemplary process 800 for de-identifying an RGB/color video captured by a 2D RGB camera installed in the OR in accordance with some embodiments described herein. In one or more embodiments, one or more of the steps in FIG. 8 may be omitted, repeated, and/or performed in a different order. Accordingly, the specific arrangement of steps shown in FIG. 8 should not be construed as limiting the scope of the technique.

Process 800 may begin by simultaneously receiving a frame of 2D color image (or simply "2D color image") in the RGB/color video from the 2D RGB camera and a corresponding depth image from a 3D depth camera, wherein the received 2D color image and the received depth image are captured at the same or substantially the same time in the OR (step 802). Next, process 800 constructs a 3D point cloud based on the received depth image by projecting the depth image into the 3D-coordinate system of the depth camera based on a known lens model of the depth camera (step 804). Note that each point in the 3D point cloud represents a 3D location on the surface of an object or a person in the OR from where the light cast by the depth camera reflects after hitting the surface of the object/person. Next, process 800 extracts a set of 3D body contours from the 3D point cloud corresponding to the bodies of the detected people in the OR (step 806). In some embodiments, to obtain the set of body contours, process 800 first identifies a set of 3D-point clusters from the 3D point cloud that potentially represent 3D objects including both non-human objects and OR personnel using a data-point clustering technique. Process 800 then identifies a subset of the set of 3D-point clusters that have high probabilities to represent human bodies use a ML human-body detection model. In various embodiments, the ML human-body detection model can be implemented using various known convolutional neural network (CNN/ConvNet) architectures. Process 800 subsequently extracts a 3D body contour from each identified cluster in the subset 3D-point clusters by identifying those surface/boundary 3D positions.

Process 800 additionally generates a set of body joints and a corresponding set of probabilities for each extracted 3D body contour by applying a ML body-joint estimation model to each identified 3D-point cluster in the subset of clusters (step 808). In various embodiments, the ML body-joint estimation model can also be implemented with known convolutional neural network (CNN/ConvNet) architectures. In some embodiments, to obtain the set of body joints for a given extracted 3D body contour, process 800 first extracts a set of shapes from the corresponding identified 3D-point cluster that was used to extract the given 3D body contour. Process 800 then computes a set of orientations of the set of extracted shapes. Process 800 subsequently estimates the set of body joints based on the set of extracted shapes and the set of computed orientations of the set of shapes. Note that each set of the extracted body joints can be used to construct a skeleton figure/representation for the detected person.

Next, process 800 projects each extracted 3D body contour in the set of body contours into a 2D body outline in the received color image and the corresponding set of 3D body joints into a 2D skeleton figure in the received color image (step 810). Note that process 800 performs the above 3D-to-2D projections by transforming each set of 3D-coordinates of a given 3D point within either the detected 3D body contour or the set of 3D body joints from the 3D-coordinate system of the 3D depth camera to a pair of 2D-coordinates in the 2D-coordinate system of the 2D RGB camera. After the transformations, both the obtained 2D body outlines and the corresponding skeleton figures can be directly overlaid onto the received 2D color image. Finally, process 800 de-identifies the received color image based on the overlaid 2D body outlines and/or the overlaid skeleton figures (step 812). Note that process 800 can blur out or otherwise obfuscate the full bodies of the detected people/personnel or selectively blur out only some portions of each detected person which are known to contain PII or potentially contain PII based on the combined information of the overlaid 2D body outline and the corresponding set of body joints/keypoints of each detected person.

Hence, at the end of step 812, the received 2D color image in the RGB/color video has been de-identified. At this point, process 800 returns to step 802 to receive the next frame of 2D color image in the RGB/color video from the RGB camera and the next frame of depth image from the depth camera, and process 800 repeats to de-identify the next frame of 2D color image. This de-identification loop of process 800 can continue de-identifying color images in the RGB/color video in the frame-by-frame manner as long as new frames of color images in the RGB/color video are still being received. However, process 800 terminates at step 812 after the last frame of 2D color image in the RGB/color video has been received and de-identified based on a corresponding received depth image from the depth camera. Note that the fully de-identified RGB/color video can then be stored, played back at a later time, further processed and/or analyzed, or uploaded to a cloud server. In some embodiments, the de-identified RGB/color video can also be displayed in real-time on a monitor in parallel with the frame-by-frame de-identification of the received real-time video images in the RGB/color video.

Although we have described de-identifying color images captured by an RGB camera using depth images captured by one depth camera, such as depth camera 630 in system 600, the disclosed systems and techniques for de-identifying color images captured by an RGB camera are not limited to a single depth camera. Without departing from the scope of the present disclosure, the disclosed systems and techniques can be extended to using two or more depth cameras for de-identifying color images captured by an RGB camera. In these embodiments, the relative position and orientation of each of the multiple depth cameras to the RGB camera need to be obtained. In some embodiments, this information can be obtained through a camera registration process for each of the multiple depth cameras during or after the depth camera installation. Note that when the relative position and orientation of each depth camera to the RGB camera are known, the inverse projection from the 3D-coordinate system of each depth camera to the 2D-coordinate system of the RGB camera will provide the correct position of the identified persons in the 2D color images. In some other embodiments, instead of the above-described one RGB camera/multiple depth camera setup, the disclosed system for de-identifying color images can include multiple RGB-D cameras installed at multiple locations in the OR, and the disclosed 2D-color-image de-identification operations can take place locally within each of the multiple RGB-D cameras. In these embodiments, it becomes possible to track the movement of a detected person in the OR by selecting one of the multiple RGB-D cameras that can provide the best viewing angle of the detected person at the current location in the OR. Moreover, when the detected person has moved to a different area of the OR, the disclosed system can switch from the currently-selected RGB-D camera to another RGB-D camera in the multiple RGB-D cameras that can provide a better viewing angle than the currently-selected RGB-D camera.

Note that the disclosed color-image de-identification system can be used for other OR workflow tracking and monitoring functions when personnel privacy is not a concern, e.g., within an internal/private system where personal-data safety is guaranteed or when personal consent to the PII is in place. In these scenarios, personnel's faces can be identified before de-identification. After the detected personnel have been individually identified, their roles and responsibilities in the OR and during a surgery can be identified and recorded, and their movements and activities can be correlated to their roles and responsibilities through the generated body-tracking data, such as the above-described body outlines and skeleton figures. Hence, the disclosed de-identification system can facilitate analyzing the OR workflow efficiency by tracking and analyzing the movements and activities of each OR staff member. This then allows the disclosed de-identification system to generate useful insight for ways to improve OR workflow efficiency and to provide real-time suggestions/feedbacks and notifications.

Figure 9:
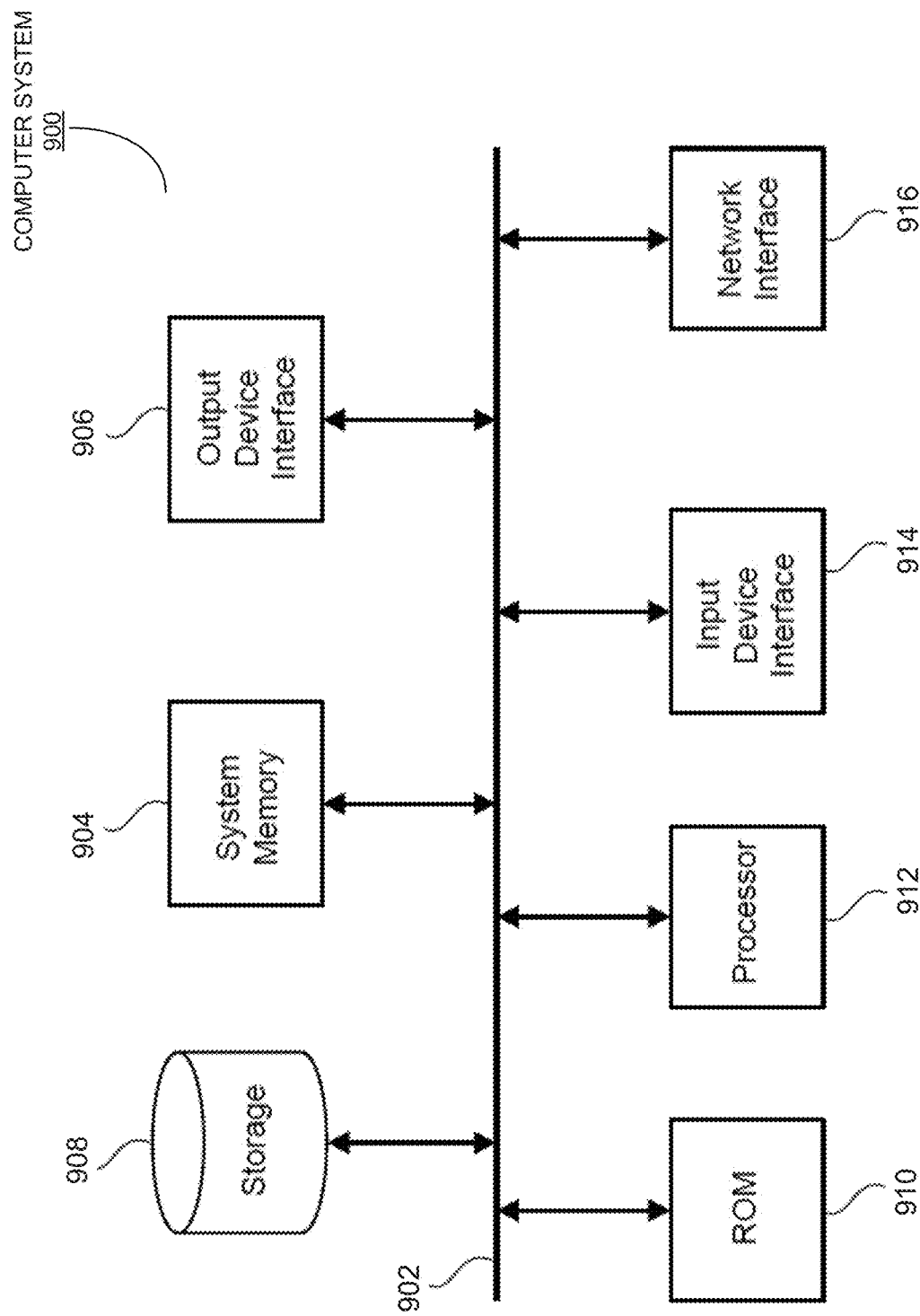
FIG. 9 conceptually illustrates a computer system with which some embodiments of the subject technology can be implemented.

FIG. 9 conceptually illustrates a computer system with which some embodiments of the subject technology can be implemented. Computer system 900 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 900 includes a bus 902, processing unit(s) 912, a system memory 904, a read-only memory (ROM) 910, a permanent storage device 908, an input device interface 914, an output device interface 906, and a network interface 916. In some embodiments, computer system 900 is a part of a robotic surgical system.

Bus 902 collectively represents all system, peripheral, and chipset buses that communicatively connect the numerous internal devices of computer system 900. For instance, bus 902 communicatively connects processing unit(s) 912 with ROM 910, system memory 904, and permanent storage device 908.

From these various memory units, processing unit(s) 912 retrieves instructions to execute and data to process in order to execute various processes described in this patent disclosure, including the depth-image-based OR target-object detection and tracking processes described in conjunction with FIGS. 1-5 and depth-image-based OR personnel de-identification processes described in conjunction with FIGS. 6-8. The processing unit(s) 912 can include any type of processor, including but not limited to, a microprocessor, a graphic processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 912 can be a single processor or a multi-core processor in different implementations.

ROM 910 stores static data and instructions that are needed by processing unit(s) 912 and other modules of the computer system. Permanent storage device 908, on the other hand, is a read-and-write memory device. This device is a non-volatile memory unit that stores instructions and data even when computer system 900 is off. Some implementations of the subject disclosure use a mass-storage device (such as a magnetic or optical disk and its corresponding disk drive) as permanent storage device 908.

Other implementations use a removable storage device (such as a floppy disk, flash drive, and its corresponding disk drive) as permanent storage device 908. Like permanent storage device 908, system memory 904 is a read-and-write memory device. However, unlike storage device 908, system memory 904 is a volatile read-and-write memory, such as a random access memory. System memory 904 stores some of the instructions and data that the processor needs at runtime. In some implementations, various processes described in this patent disclosure, including the depth-image-based OR target-object detection and tracking processes described in conjunction with FIGS. 1-5 and depth-image-based OR personnel de-identification processes described in conjunction with FIGS. 6-8, are stored in system memory 904, permanent storage device 908, and/or ROM 910. From these various memory units, processing unit(s) 912 retrieves instructions to execute and data to process in order to execute the processes of some implementations.

Bus 902 also connects to input and output device interfaces 914 and 906. Input device interface 914 enables the user to communicate information to and select commands for the computer system. Input devices used with input device interface 914 include, for example, alphanumeric keyboards and pointing devices (also called "cursor control devices"). Output device interface 906 enables, for example, the display of images generated by computer system 900. Output devices used with output device interface 906 include, for example, printers and display devices, such as cathode ray tubes (CRT) or liquid crystal displays (LCD). Some implementations include devices such as a touchscreen that functions as both input and output devices.

Finally, as shown in FIG. 9, bus 902 also couples computer system 900 to a network (not shown) through a network interface 916. In this manner, the computer can be a part of a network of computers (such as a local area network ("LAN"), a wide area network ("WAN"), an intranet, or a network of networks, such as the Internet. Any or all components of computer system 900 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. The terms "disk" and "disc," as used herein, include compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can, in some cases, be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for identifying and tracking a target object being a person in an operating room (OR) and de-identifying a color video captured by a 2D camera, the method comprising:
    receiving a 2D color image captured by a 2D camera and a depth image among a sequence of depth images captured by a depth camera both cameras operating simultaneously and installed in the OR;
    identifying a set of potential target points in the received depth image that potentially belongs to the target object based on one or more target object criteria;
    extracting one or more object clusters from the set of potential target points using a data-point clustering technique;
    identifying the target object from the extracted one or more object clusters as a body of a person and extracting a 3D body contour from the extracted one or more clusters;
    projecting the 3D body contour into a 2D body outline in the received 2D color image;
    overlaying the 2D body outline onto the received 2D color image; and
    de-identifying the received 2D color image based on the overlaid 2D body outline.

2. The computer-implemented method of claim 1, wherein prior to identifying the set of potential target points, the method further comprises generating a three-dimensional (3D) point cloud based on the received depth image by projecting each 2D pixel (u, v) and the corresponding distance value d (u, v) in the depth image into a 3D point in a 3D-coordinate system aligned with the depth camera.

3. The computer-implemented method of claim 2, wherein the method further comprises, for each 3D point in the 3D point cloud:
    computing a surface orientation at the 3D point based on one or more vector cross-products between two or more edges formed by the 3D point and two or more neighboring 3D points of the 3D point in the 3D point cloud; and
    associating the computed surface orientation with the 3D coordinates of the 3D point.

4. The computer-implemented method of claim 3, wherein identifying the set of potential target points in the 3D point cloud that potentially belongs to the target object based on one or more target object criteria include:
    transforming each 3D point and the associated surface orientation in the 3D point cloud into a 3D-coordinate system aligned with the ground surface of the OR; and
    extracting the set of 3D potential target points from the transformed 3D point cloud by filtering the transformed 3D point cloud base on one or more geometrical criteria of the target object.

5. The computer-implemented method of claim 1 further comprising:
    generating a set of 3D body joints for the extracted 3D body contour;
    projecting the set of 3D body joints into a 2D skeleton figure in the received 2D color image; and
    overlaying the 2D skeleton figure onto the received 2D color image, wherein de-identifying the received 2D color image is further based on the overlaid 2D skeleton figure.

6. The computer-implemented method of claim 1, wherein the data-point clustering technique is a Density-Based Spatial Clustering of Applications with Noise (DBSCAN) clustering technique which is configured to identify a cluster of target points in the set of potential target points having a higher density than the remainder of the set of potential target points.

7. The computer-implemented method of claim 1, wherein identifying the target object from the extracted one or more object clusters includes:
    for each object cluster in the extracted one or more object clusters,
        generating a minimum bounding box for the object cluster; and
        determining whether the object cluster is the target object by comparing the dimensions of the generated minimum bounding box against the dimensions of the target object.

8. The computer-implemented method of claim 7, wherein determining whether the object cluster is the target object further includes applying one or more additional detection requirements listed below:
    determining whether the number of data points inside the generated minimum bounding box satisfies a number-of-points requirement of the target object;
    determining whether the orientation of the generated minimum bounding box satisfies a surface orientation requirement of the target object; and
    determining whether the position of the generated minimum bounding box satisfies a position requirement of the target object.

9. The computer-implemented method of claim 1, wherein after installing the depth camera, the method further comprises calibrating the depth camera to obtain the position and the orientation of the depth camera with respect to a ground surface in the OR.

10. The computer-implemented method of claim 1, wherein after identifying the target object from the extracted one or more object clusters, the method further comprises tracking the identified target object by:
    determining if the identified target object has been previously-identified in one or more preceding depth images in the sequence of depth images; and if so, estimating a movement of the identified target object;

otherwise, determining that the identified target object is a newly-identified target object not previously identified.

11. An apparatus for identifying and tracking a target object being a person in an operating room (OR) and de-identifying a color video captured by a 2D camera, the apparatus comprising:
one or more processors; and
a memory coupled to the one or more processors, the memory storing instructions that, when executed by the one or more processors, cause the apparatus to:
receive a 2D color image captured by a 2D camera and a depth image among a sequence of depth images captured by a depth camera both cameras operating simultaneously while installed in the OR;
identify a set of potential target points in the received depth image that potentially belongs to the target object based on one or more target object criteria;
extract one or more object clusters from the set of potential target points using a data-point clustering technique;
identify the target object from the extracted one or more object clusters as a body of a person and extract a 3D body contour from the extracted one or more clusters;
project the 3D body contour into a 2D body outline in the received 2D color image;
overlay the 2D body outline onto the received 2D color image; and
de-identify the received 2D color image based on the overlaid 2D body outline.

12. The apparatus of claim 11, wherein prior to identifying the set of potential target points, the memory further stores instructions that, when executed by the one or more processors, cause the apparatus to generate a three-dimensional (3D) point cloud based on the received depth image by projecting each 2D pixel (u, v) and the corresponding distance value d(u, v) in the depth image into a 3D point in a 3D-coordinate system aligned with the depth camera.

13. The apparatus of claim 12, wherein the memory further stores instructions that, when executed by the one or more processors, cause the apparatus to:
compute a surface orientation, at each 3D point in the 3D point cloud, based on one or more vector cross-products between two or more edges formed by the 3D point and two or more neighboring 3D points of the 3D point in the 3D point cloud; and
associate the computed surface orientation at each 3D point in the 3D point cloud with the 3D coordinates of the 3D point.

14. The apparatus of claim 13, wherein the memory further stores instructions that, when executed by the one or more processors, cause the apparatus to identify the set of potential target points in the 3D point cloud based on one or more target object criteria by:
transforming each 3D point and the associated surface orientation in the 3D point cloud into a 3D-coordinate system aligned with the ground surface of the OR; and
extracting the set of 3D potential target points from the transformed 3D point cloud by filtering the transformed 3D point cloud base on one or more geometrical criteria of the target object.

15. The apparatus of claim 14, wherein the memory further stores instructions that, when executed by the one or more processors, cause the apparatus to:
generate a set of 3D body joints for the extracted 3D body contour;
project the set of 3D body joints into a 2D skeleton figure in the received 2D color image; and
overlay the 2D skeleton figure onto the received 2D color image, wherein de-identifying the received 2D color image is further based on the overlaid 2D skeleton figure.

16. The apparatus of claim 11, wherein the memory further stores instructions that, when executed by the one or more processors, cause the apparatus to identify the target object from the extracted one or more object clusters by:
for each object cluster in the extracted one or more object clusters,
generating a minimum bounding box for the object cluster; and
determining whether the object cluster is the target object by comparing the dimensions of the generated minimum bounding box against the dimensions of the target object.

17. A system for identifying and tracking a target object being a person in an operating room (OR) and de-identifying a color video captured by a 2D camera, the system comprising:
a depth camera installed in the OR;
a 2D camera installed in the OR;
one or more processors coupled to the depth camera and to the 2D camera;
a memory coupled to the one or more processors, the memory storing instructions that, when executed by the one or more processors, cause the system to:
receive a 2D color image captured by the 2D camera and a depth image among a sequence of depth images captured by the depth camera both cameras operating simultaneously;
identify a set of potential target points in the received depth image that potentially belongs to the target object based on one or more target object criteria;
extract one or more object clusters from the set of potential target points using a data-point clustering technique;
identify the target object from the extracted one or more object clusters as a body of a person and extract a 3D body contour from the extracted one or more clusters;
project the 3D body contour into a 2D body outline in the received 2D color image;
overlay the 2D body outline onto the received 2D color image; and
de-identify the received 2D color image based on the overlaid 2D body outline.

18. The system of claim 17, wherein the memory further stores instructions that, when executed by the one or more processors, cause the system to:
generate a set of 3D body joints for the extracted 3D body contour;
project the set of 3D body joints into a 2D skeleton figure in the received 2D color image; and
overlay the 2D skeleton figure onto the received 2D color image, wherein de-identifying the received 2D color image is further based on the overlaid 2D skeleton figure.

* * * * *